United States Patent [19]
Schuhmann et al.

[11] Patent Number: 5,942,904
[45] Date of Patent: Aug. 24, 1999

[54] MOISTURE SENSOR FOR LARGE AREA LAYERS

[75] Inventors: Rainer Schuhmann; Alexander Brandelik, both of Karlsruhe; Christof Hübner, Edingen-Neckarhausen, all of Germany

[73] Assignee: Forschungszentrum Karlsruhe GmbH, Karlsruhe, Germany

[21] Appl. No.: 08/880,772

[22] Filed: Jun. 23, 1997

Related U.S. Application Data

[63] Continuation-in-part of application No. PCT/EP96/00010, Jan. 4, 1996, abandoned.

[30] Foreign Application Priority Data

Jan. 17, 1995 [DE] Germany ............... 195 01 196

[51] Int. Cl.⁶ ............................................. G01R 27/32
[52] U.S. Cl. ...................... 324/648; 324/533; 340/604
[58] Field of Search ........................... 324/532, 533, 324/534, 535, 722, 648; 73/73; 340/604

[56] References Cited

U.S. PATENT DOCUMENTS

| | | |
|---|---|---|
| 4,341,112 | 7/1982 | Mackay et al. . |
| 5,155,356 | 10/1992 | Peters et al. . |
| 5,177,996 | 1/1993 | Sahakian ................... 324/533 |
| 5,376,888 | 12/1994 | Hook ....................... 324/534 |
| 5,410,255 | 4/1995 | Bailey ..................... 324/534 |

*Primary Examiner*—Maura Regan
*Attorney, Agent, or Firm*—Klaus J. Bach

[57] ABSTRACT

In a moisture sensor arrangement for large area layers including a high-frequency electrical generator, a signal travel time measuring apparatus and a reflectometer, all connected to a cable system, at least two independent cables of the cable system are arranged so as to have cross-over points with, and being disposed in spaced relationship but sufficiently close t, one another such that a signal transfer can occur at the cross-over points.

5 Claims, 2 Drawing Sheets

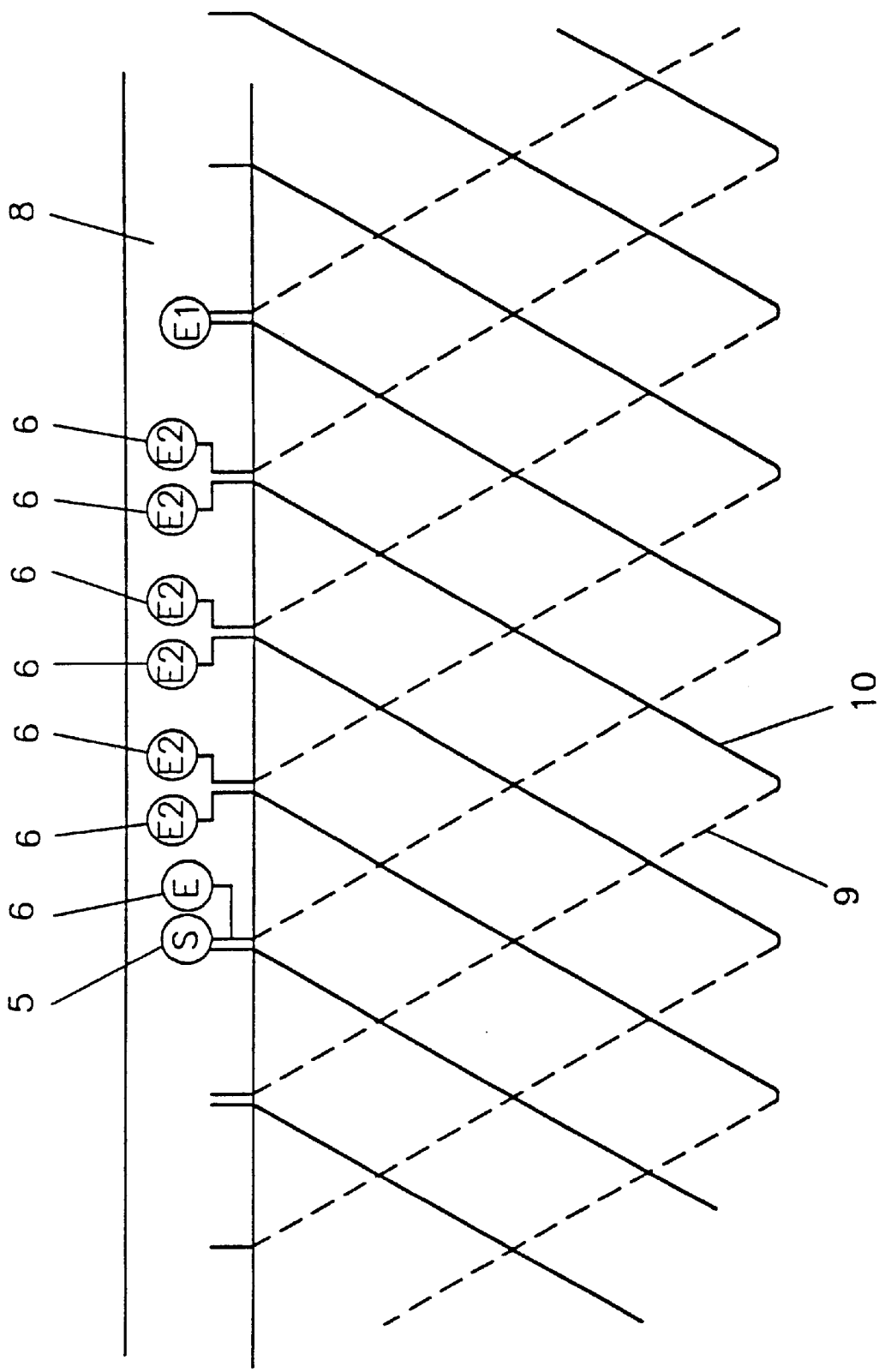

MOISTURE SENSOR FOR LARGE AREA LAYERS

This is a Continuation-In-Part application of international patent application PCT/EP96/00010 filed Jan. 4, 1996 now abandoned and claiming priority of German patent application No. 193 01 196.1 of Jan. 17, 1995.

BACKGROUND OF THE INVENTION

The invention relates to a moisture sensor for large-area layers utilizing conductors disposed in the layers.

Waste deposits generally have clay-mineral bottom layers providing a seal to prevent leaching of the waste by rain and the passage of leach water into the ground water. These sealing layers, that is, the base seal layer at the bottom as well as the cover layer on top are resilient so that they can follow any deformation of the whole waste pile and remain sealed for many decades. However, the sealing layer may rupture by uncontrollable shearing stresses. Also, a relatively small loss of moisture (about 4–5%) from this highly densified and almost saturated mineral protective layer results in a loss of its ability to provide water insulation. An early recognition and localization of a possible fracture or drying out of a damaged area is therefore of great environmental and economical importance. The usual perk tests made today indicate a damage too late and do not permit to determine the location of the damaged area. A reproducible location indicating measurement of the moisture and the density of the sealing layer is required, but is not available up to this date.

In farm and nursery operations, an optimal irrigation depends on the moisture measurement of a large ground area with a high local resolution. Too little irrigation causes damage to the plants, too much irrigation results in washing away of nutrients and in salt deposits.

In large grain storage areas, it is important to monitor the moisture of the whole volume of stored grain. Samples taken from the surface or measurements taken on the surface provide insufficient measurement accuracies.

Meteorological models require an accurate knowledge of the water content of the soils since the energy exchange between the ground and the atmosphere occurs mainly by evaporation and condensation of water. This involves particularly the layers close to the surface.

For moisture measurements, generally probes are used which determine the dielectric coefficient DK of the mixture to be tested. From this, the moisture can be determined with the aid of calibration measurements. A particular procedure which is in use is a time-based signal reflection method, which, in the technical literature, is generally called "Time-Domain-Reflectometry" method or abbreviated "TDR" method.

This method is based on the travel of electromagnetic waves in conductors. The electric properties of conductors and, consequently, the signal transmission characteristics are defined, among others, by the characteristic impedance the attenuation, and the travel speed of the signal. As is well known, these values depend (possibly with losses) on the dielectric properties of the ambient space in which the electric field extends. This space is limited in co-axial conductors by the outer shielding. In open conductor systems such as the double conductors (Lecher-conductor), the triple or multiple conductor and the surface wave guide (for example, according to Gouban), however the field extends beyond the close surroundings of the conductor. A change in the material properties in that area also changes the signal transmission properties of the conductor.

The Time Domain Reflectometry (TDR) method for measuring the moisture content in soils is known from the publication "Wasser & Boden" (R. Rook, S. Melchior, G. Miehlich, "DIE TIME DOMAIN REFLECTOMETRY (TDR) FÜR WASSERGEHALTSMESSUNG IN BÖDEN", Wasser & Boden, Nov. 4, 1993). The probe disclosed therein is based, among others, on the sensor introduced by Davis et al., (J. L. Davis, A. P. Amman, "ELECTROMAGNETIC DETECTIONS OF SOIL MOISTURE", Canadian Journal of Remote Sensing, Vol. 3, No. 1, 1977a).

A disadvantage of this sensor is the short measurement length of the measurement fork forming an open conductor. Generally, TDR probes are made and offered in lengths of only a few 10 centimeters. It is also disadvantageous that different layers along the probe rod can average out the results. Multiple reflections can neutralize one another. Also, the relative high electric conductivity limits the application to a few centimeters because of a high conductor attenuation. Another disadvantage is that the fork may spread apart when it is inserted into a mixture. The impedance increase resulting therefrom indicates a drier state than is actually present. The dielectricity coefficient of water is degraded greatly at frequencies greater than 1 GHz. This degradation is subject to many additional factors. In order to obtain an accurate correlation between the DK and the moisture content the measuring frequency (and consequently, the ramp steepness of a measuring pulse) must be limited to less than 1 GHz. The TDR probes known so far unfortunately have no such limitation.

It is the object of the present invention to provide a sensor of the type described above which however covers a relatively large area and has a good location resolution.

SUMMARY OF THE INVENTION

In a moisture sensor arrangement for large area layers including a high-frequency electrical generator, a signal travel time measuring apparatus and a reflectometer, all connected to a cable system, at least two independent cables of the cable system are arranged so as to have cross-over points with, and being disposed in spaced relationship but sufficiently close t, one another such that a signal transfer can occur at the cross-over points.

It is advantageous to use a double conductor with a continuous or interrupted web therebetween which insures a constant cable impedance and which has the result that only a part of the electrical field extends into the material to be measured.

The invention will be described below on the basis of a particular embodiment with reference to the drawings.

BRIEF DESCRIPTION OF THE DRAWINGS

FIGS. 2 and 3 show exemplary arrangements with several intersecting conductor systems.

DESCRIPTION OF A PREFERRED EMBODIMENT

Figure 1:
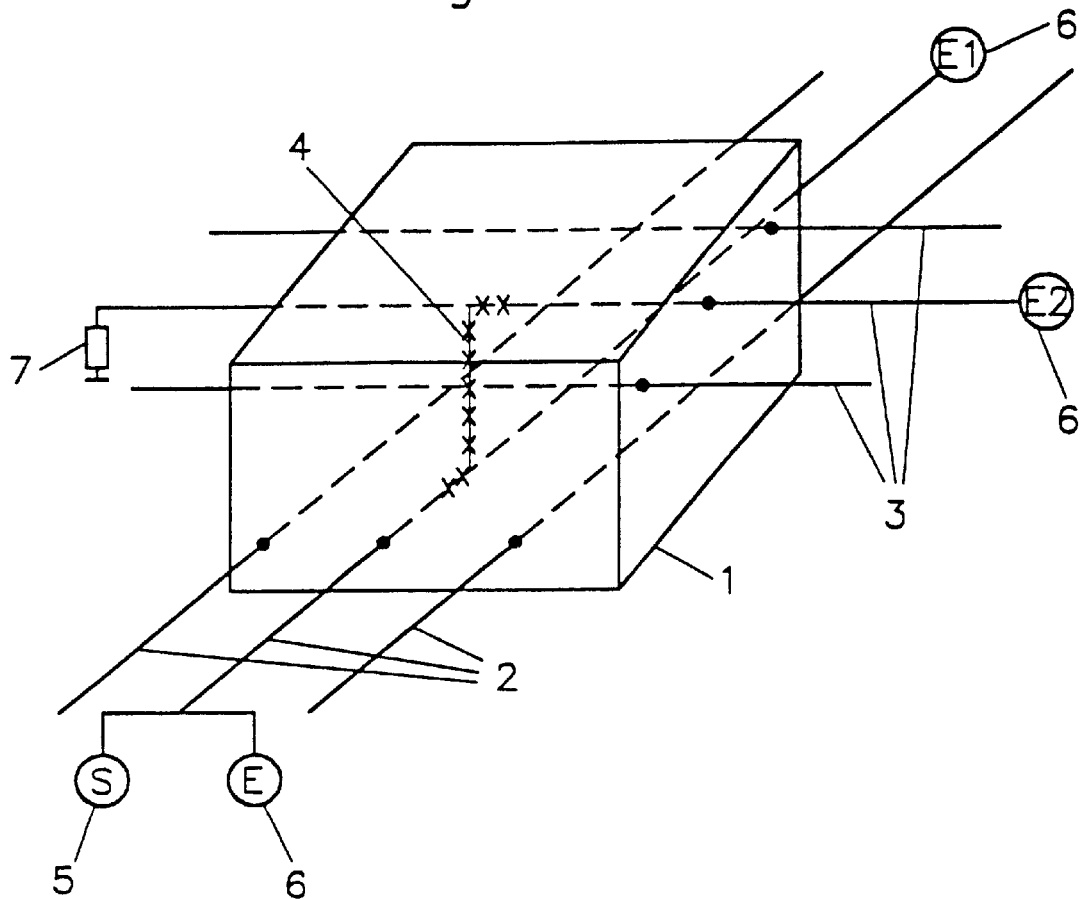
FIG. 1 shows a portion of a measuring arrangement in an area where several conductors intersect.

FIG. 1 shows a section 1 of a material layer whose moisture content and density are measured. Measuring cables 2 which preferably include double conductors are disposed in a lower plane of the material layer section 1. Cables 3 extend in a higher layer in another direction such that the cables 2 and 3 are arranged in spaced planes. The cables 2 and 3 do not touch each other at the crossing points.

Each of the independent cables is a flat cable with two or more conductors spaced from one another by intermediate web portions and having a predetermined constant wave impedance. At the points of intersection, the cables of the different planes are at such a distance from one another that a signal transfer can occur in the area 4 of the intersection of the independent cables. The signal transfer between two cables in the area 4 of an intersection (shown by small crosses) can be increased if the angle of intersection deviates from a 90° angle.

If a large crack occurs in the material layer section 1, the cable will break. In a first measuring step, the cable 2 is checked for an interruption by way of a reflection test which is performed with a signal generator 5 and a receiver E6 synchronized therewith. This measurement can also be performed with a reflectometer. The location of the interruption can be calculated from the time behavior of the reflection signal. A second measurement determines whether an impedance change has occurred along the cable 2. This measurement can be made by a travel time determination between the generator 5 and the receiver E1, 6. In a dry area, the travel time will be shorter and the impedance will be greater than normal. If the impedance changes along the cable 2, the receiver E2 is switched to a crossing cable 3 and another measurement is performed.

The signal transfer permits the reception at one of the cables 3. The switch-over of the receiver E2, 6 to cables 3, which are closer to the signal generator distinguishes eventually those areas which have caused several impedance changes in the cable 2. The determination of the changes of the DK occurs by travel time and impedance measurements. In this way, the measurement accuracy is increased. By permutation of those areas of the signal generator 5 and the receiver E6 each desired area of the network comprising the cable 2 and the cables 3 which extend in different directions can be measured. The signal generator 5 is limited in its frequency to 1 GHz for the reason mentioned above. A measurement cable 3 has at both ends an impedance 7 with the expected conductor impedance value.

A particular advantage of this measurement arrangement resides in the very low price of the cable installed in the ground (about 6 cents per m) which makes a permanent large-area surveillance economically feasible.

Figure 2:
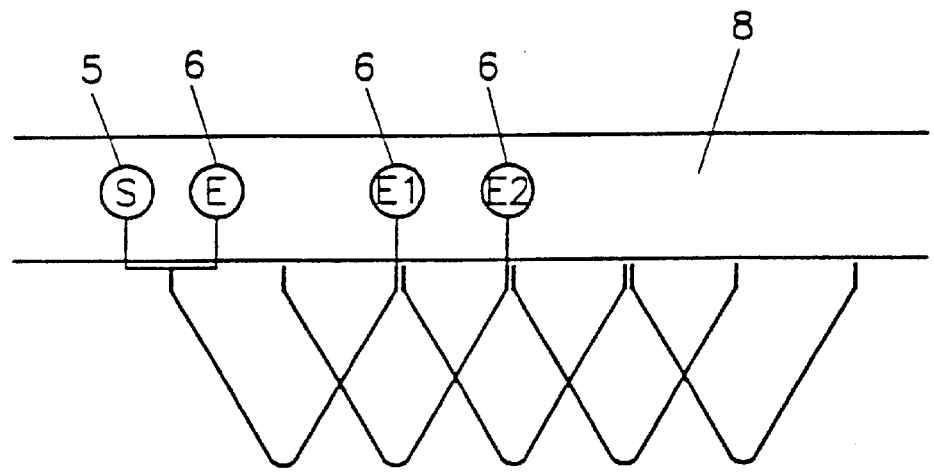

FIG. 2 shows a system of independent cables of which each one crosses at most two other cables and wherein all connection points for the generator 5 and the receiver E are accessible from a single service path 8.

In the arrangement of FIG. 3, the cables have a substantially larger number of crossing points with adjacent cables. Also, the cable halves 9 shown by dashed lines are at a lower elevation than the parts 10 shown in full lines. In this way, the depth resolution in the whole layer is increased since the two cable halves 9, 10 serve the detection each in a partial layer within the range of the penetration depth of the field. Any area with a fault which is disposed for example between the sender 5 and the receiver E1 can be localized more distinctly by a switch-over to one of the receivers E2 in the indicated positions where the respective cables cross. The resolution can be further improved by providing an arrangement with more cross-over points between the various cables.

The cables may also be so installed that more than two partial layers can be covered by the detection system by providing several conductor levels on top of one another.

Actual measurements were taken with two different types of cables: A flat conductor with 240Ω impedance: This kind of cable was used earlier as television antenna cable. In wet soils, it showed an attenuation of 0.6 dB/m, a travel time change of 90% and an impedance change of 97% with respect to air. Web conductor with 440Ω impedance: this cable showed in the same wet soil on attenuation of 0.4 dB/m, a travel time change of 120% and an impedance change of 160% with respect to air. The signal transfer attenuation for the first cable was about −26 dB and for the second cable only about −20 dB. These data show that a length with a single signal transfer may be about 70 m.

What is claimed is:

1. A moisture sensor for large area layers comprising: at least one high frequency electrical signal generator, a signal travel time measuring apparatus, a reflectometer and a cable system connected to said high frequency electrical signal generator for receiving high frequency electrical signals therefrom, to said signal time measuring apparatus for determining impedance changes in said cable systemm, and to said reflectometer for determining reflection travel times of said signal in said cable system, said cable system comprising at least two independent cables arranged in said layers in different planes and extending at different angles so as to have cross-over points which are spaced from one another but where said independent cables are sufficiently close to one another that a signal transfer between the crossing cables can occur at the cross-over points dependent on the moisture content of said layers at said cross-over points.

2. A moisture sensor according to claim 1, wherein said independent cables of said cable system include Lecher-type two-conductor cables.

3. A moisture sensor according to claim 1, wherein one of the cables of said cable system has cross-over points with several independent cables of the cable system with predetermined distances between the various cross-over points.

4. A moisture sensor according to claim 1, wherein said cables are disposed in a layer to be surveyed in a net-like fashion.

5. A moisture sensor according to claim 1, wherein all cables of the cable system excited by signal transfer from another cable are provided with fitted end portions at both ends.

* * * * *